United States Patent [19]
Kantor

[11] Patent Number: 5,708,696
[45] Date of Patent: Jan. 13, 1998

[54] POSITIONING DEVICE FOR AN X-RAY MACHINE

[75] Inventor: Arkady Kantor, Buffalo Grove, Ill.

[73] Assignee: Dentsply Research & Development Corp., Milford, Del.

[21] Appl. No.: 715,156

[22] Filed: Sep. 17, 1996

[51] Int. Cl.⁶ ............................................. A61B 6/08
[52] U.S. Cl. .................................. 378/206; 378/205
[58] Field of Search ................................ 378/206, 205, 378/64, 65

[56] References Cited

U.S. PATENT DOCUMENTS

| | | | |
|---|---|---|---|
| 1,976,179 | 10/1934 | Mannl | 250/34 |
| 2,806,146 | 10/1957 | Thomspson | 250/105 |
| 3,156,824 | 11/1964 | Peyser | 250/105 |
| 3,163,762 | 12/1964 | Peyser | 250/105 |
| 3,767,931 | 10/1973 | Williams | 378/206 |
| 3,864,576 | 2/1975 | Stevenson | 250/505 |
| 4,167,675 | 9/1979 | Stodberg | 250/491 |
| 4,603,427 | 7/1986 | Alpern et al. | 378/150 |
| 4,670,896 | 6/1987 | Klausz | 378/206 |
| 5,033,074 | 7/1991 | Cotter et al. | 378/147 |
| 5,438,991 | 8/1995 | Yu et al. | 128/653.1 |

FOREIGN PATENT DOCUMENTS 2 614 491   10/1988   France .

*Primary Examiner*—Don Wong
*Attorney, Agent, or Firm*—Douglas J. Hura; James B. Bieber

[57] ABSTRACT

A device (10) for positioning the location of an emitted x-ray (1 2a) has an optical mirror (20) having at least two leg portions (31, 32) separated by stepped portion (30) formed therewith. Leg portions (31, 32) and stepped portion (30) have substantially uniform x-ray transmisivity. A light emitting assembly (21) for transmitting a locating beam of light (14) onto the stepped portion (30). The device also includes mounting means (13, 22) for mounting the optical mirror (20) proximate to the x-ray emitting device (11) and completely encompassing the emitted x-ray (12a). The locating beam of light (14) is caused to be directed toward the target (15) by the angle of the mirror (20).

9 Claims, 2 Drawing Sheets

POSITIONING DEVICE FOR AN X-RAY MACHINE

TECHNICAL FIELD

The present invention is directed toward a positioning device for an x-ray machine to align the path of emitted x-rays. More particularly, the invention includes an optical mirror having an angled or stepped portion therein, such that an emitted light beam is reflected from the optical mirror to be projected upon an x-ray target. The optical mirror is transmissive to the emitted x-ray and encompasses the x-ray.

BACKGROUND OF THE INVENTION

X-ray devices have had widespread use in the diagnosis and treatment of dental and medical conditions and in many industrial applications. For many reasons, the more precise the alignment of the emitted x-ray to its intended target, the better is the resulting image. X-rays themselves are not within the human visible light spectrum and therefore it is often difficult to properly align the direction of the emitted x-ray with any precision.

Perhaps more importantly, especially for dental and medical usage, a more precise alignment of the x-ray means that a smaller x-ray field needs to be emitted than if the target is not so efficiently aligned. The less the amount of the emitted x-ray, the less amount of energy the patient absorbs. This is desirable because x-ray energy poses health risks.

There have been a number of attempts to provide x-ray emitting devices with targeting or positioning capabilities. These have included mechanical arms extending from the x-ray machine itself, as shown in U.S. Pat. No. 4,603,427. It was also known at one time to replace the x-ray emitter itself with a visible light emitting bulb, align the x-ray with the visible light and then replace the light bulb with the x-ray emitter. This was a time consuming process and did not ensure a proper alignment.

Another type of known device includes a light emitting source placed within the emitted x-ray field, as in for example, French Pat. No. 2,614,431. The light source is used to align the device and is then removed from the x-ray field prior to the x-ray being taken. If left in the emitted x-ray field during the x-ray session, the light emitting device would absorb x-rays which would detrimentally affect the produced image.

Perhaps one of the more successful aligning devices has included the angled mirror type as shown for example, in U.S. Pat. Nos. 1,976,179 and 3,156,824. These devices have been generally limited to providing a broad field of light projected onto a target, at best limited to the cone of the emitted x-rays. Thus, while an improvement over the other aligning devices and methods, these devices have not allowed for precise alignment such as when required for diagnosis or treatment of a small target such as a tooth, a small tumor or the like. Further, many of the mirrors and their support structures also are located within the x-ray cone itself, resulting in shadows upon the resulting image.

A need exists therefore, for a device to precisely align the position of an emitted x-ray. The device should be capable of more precise alignment than just visibly projecting the entire x-ray cone field and should not cast abnormal shadows onto any particular area of the resulting image.

SUMMARY OF THE INVENTION

It is therefore, an object of the present invention to provide a device for aligning the path of an x-ray emission.

It is another object of the invention to provide such a device which permits precise alignment of the x-ray.

It is a further object of the invention to provide a device as above which does not detrimentally affect the image produced by the x-ray.

These and other objects of the invention which shall become apparent from the present discussion and the following specification are accomplished by the invention as hereinafter described and claimed.

In general, a device for positioning the location of an x-ray emitted from an x-ray emitting device and relative to an x-ray target, comprises an optical mirror having at least two leg portions separated by a stepped portion integrally formed with the leg portions and positioned at a predetermined angle thereto. The leg portions and stepped portion have substantially uniform x-ray transmissivity. The device also includes a light emitting means for transmitting a locating beam of light onto the stepped portion of the optical mirror, and mounting means for mounting the optical mirror proximate to the x-ray emitting device and completely encompassing the emitted x-ray. The locating beam of light is caused to be directed toward the x-ray target based upon the predetermined angle.

There is also provided according to the invention, an improved dental x-ray positioning device of the type having an optical mirror placed at an angle within an x-ray emission, and having a remote light source for projecting a light beam onto the optical mirror. The improvement comprises an optical mirror being positioned to completely encompass the emitted x-ray, wherein the optical mirror has first and second leg portions separated and connected by an integrally formed angled and stepped portion. The first and second leg portions and the stepped portion have a substantially uniform transmissivity to the x-ray emission.

The invention also includes a method of aligning the path of an x-ray emission relative to an x-ray target, which comprises the steps of providing an optical mirror having first and second leg portions separated and connected by a stepped portion at a predetermined angle thereto, and projecting a light beam onto the stepped portion such that the light beam is reflected from the stepped portion and is projected upon an x-ray target.

PREFERRED EMBODIMENT FOR CARRYING OUT THE INVENTION

Figure 1:
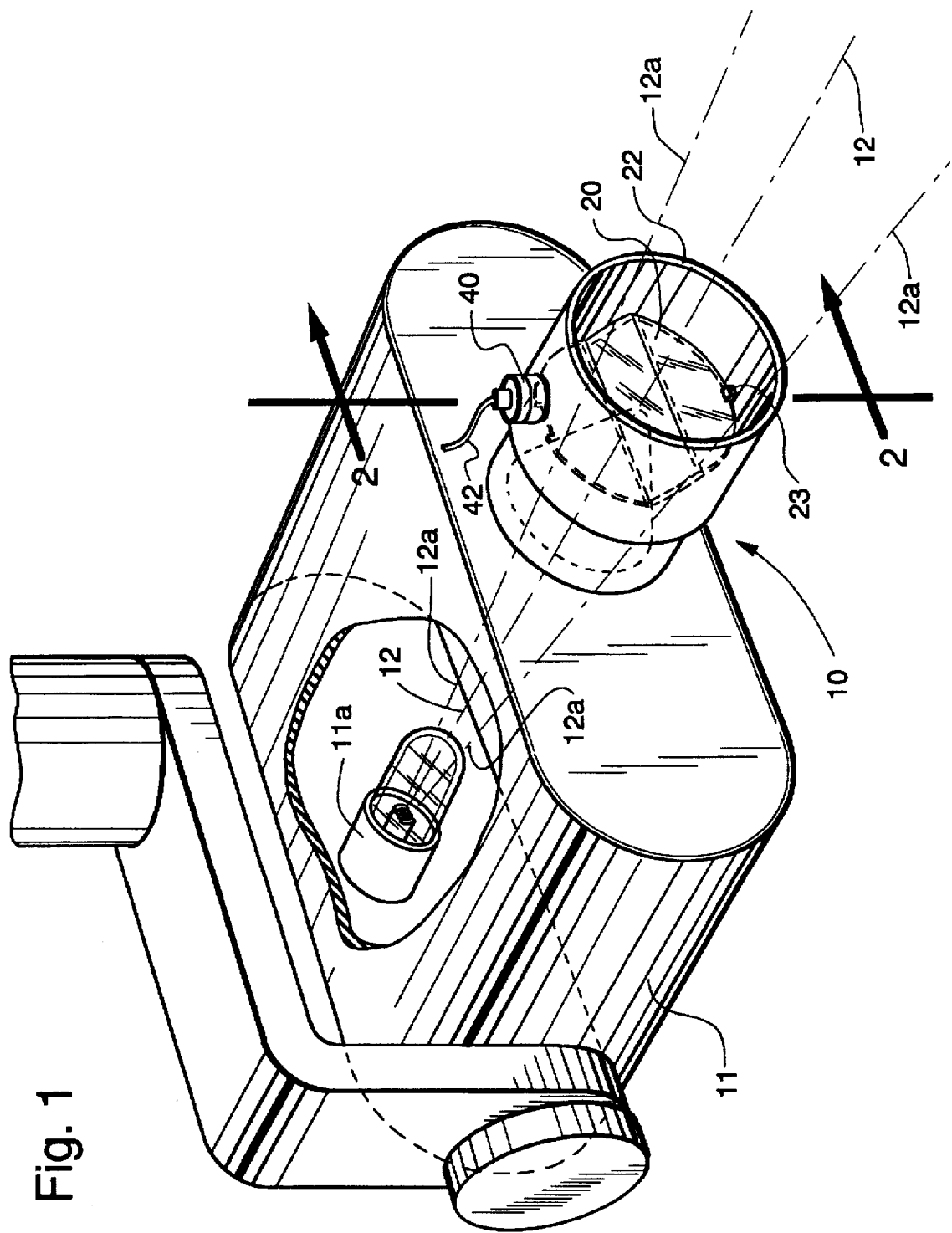
FIG. 1 is a partially broken away perspective view of a device for positioning the path of an emitted x-ray according to the concepts of the present invention, shown for environmental purposes as attached to a dental x-ray machine.

A positioning device for an x-ray machine is generally designated by the number 10 on the attached drawings. For environmental purposes, positioning device 10 is shown attached to a dental x-ray machine 11. While the present invention is particularly suitable for use with dental x-ray machines, it will be understood that it can be used with any medical, industrial and other type of x-ray machines, and in any application where precise alignment of any type is required. For the sake of this disclosure, the use of "x-ray", "x-ray machine", "dental x-ray" or any similar designation is understood to include all such applications without limitation. X-ray machine 11 is a standard x-ray device having an x-ray emitter 11a for emitting an x-ray cone as will be understood by those skilled in the art. Such an x-ray cone has an axial center designated by the line 12 on the drawings, and the emitted x-ray cone itself is generally designated by the number 12a on the drawings.

Figure 2:
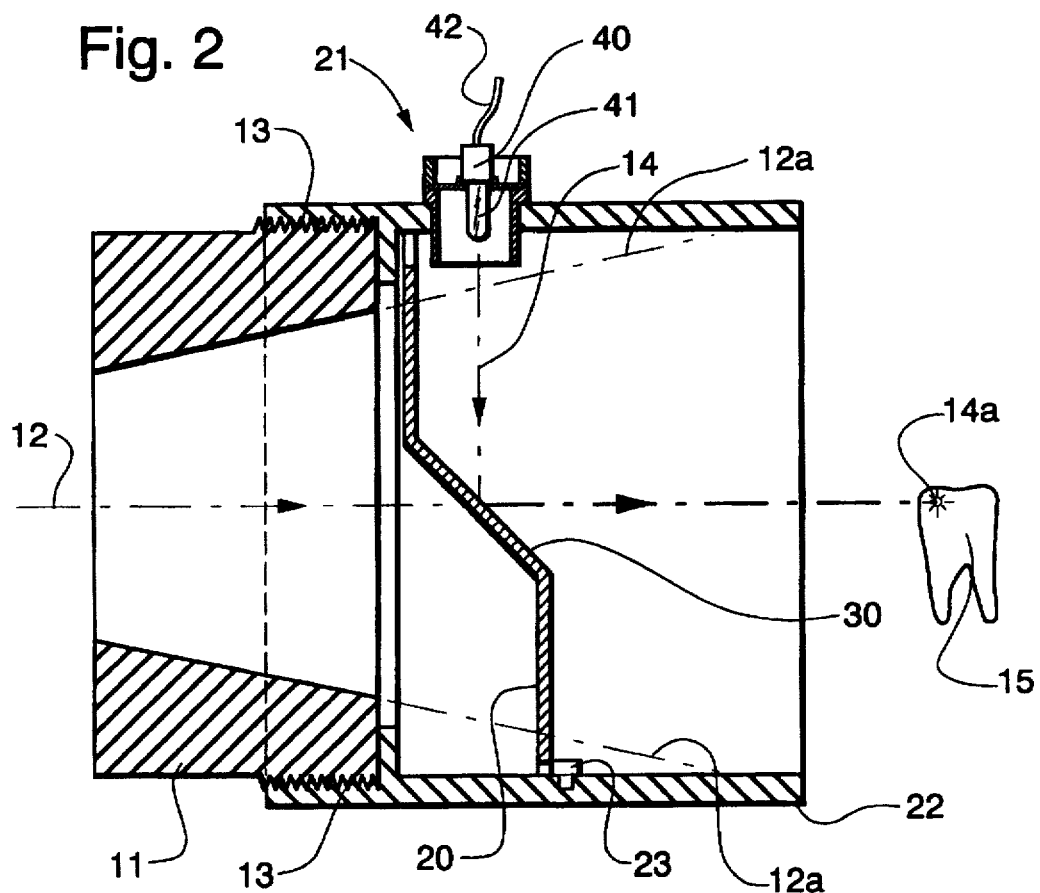
FIG. 2 is a cross-sectional view taken along line 2—2 of FIG. 1.
Figure 3:
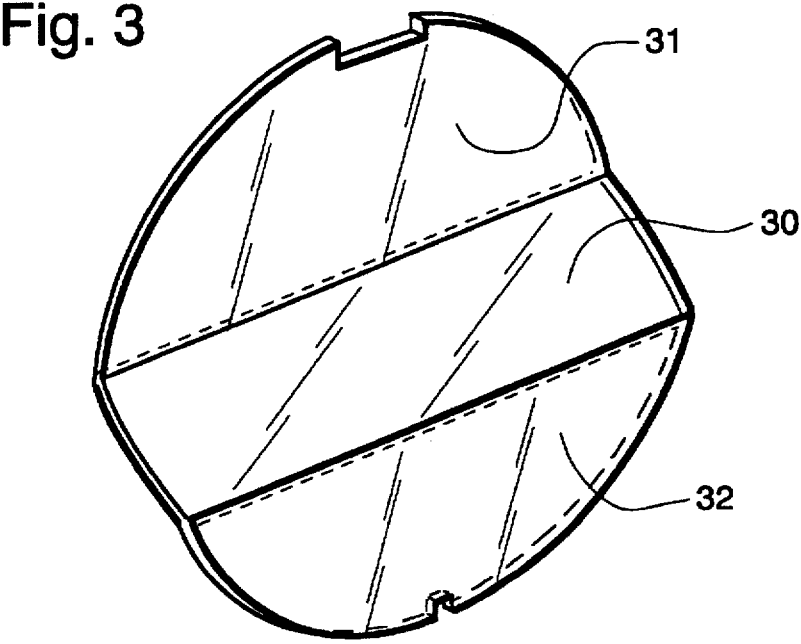
FIG. 3 is a perspective view of one portion of the cross sectional view of FIG. 2, namely the optical mirror.

Positioning device 10 includes a means of being mounted to the x-ray machine 11, such as mating threads 13 between positioning device 10 and x-ray machine 11 (FIG. 2). Mounting threads 13 can be replaced with a snap fit, friction fit, integral molding, or any other means of mounting positioning device 10 to x-ray machine 11 (FIG. 2). When positioning device 10 is fitted as an after-market add on, it desirably replaces the standard x-ray machine cone (not shown) by whatever means was used to secure that original cone.

As shown in FIG. 2, positioning device 10 causes a focused beam of light 14 to shine onto a target such as tooth target 15 of which an image is to be taken by the emitted x-ray, that is the target 15 to be "x-rayed". As will be more fully explored below, by "focused" beam of light it is meant one where the beam is made up of converging waves of light or generally parallel waves, or gradually diverging waves such that the waves are substantially parallel at the target 15. Preferably, the focused beam 14 is generally the same size as the target 15 or smaller than the target 15. For example only, in the case of a dental x-ray device 11, the size of the focused beam 14 would be from about 0.375 or lower to about 0.5 or larger inches in diameter. It will also be appreciated that this is a general designation and that the beam 14 need not be of any particular shape or size. The more narrow the beam 14 however, the more precise can be the alignment of x-ray machine 11. It is also preferred that beam 14 be projected such that it is generally located at the axial center 12 of the emitted x-ray cone 12a, as will also be more fully explored hereinbelow. Light beam 14 projects a positioning dot 14a upon target 15 which is thereby aligned with the axial center of x-ray cone 12a.

With reference to FIG. 2, positioning device 10 includes an optical mirror 20, a light beam emitting device assembly generally designated by the number 21 and a main housing 22. Preferably, main housing 22 includes means for mounting mirror 20 such as thread means 13 for mounting mirror 20 proximate to x-ray machine 11. The means for mounting mirror 20 may include any such means including mechanical brackets or other fastening deices, adhesive bonding or welding, or any such means. One particularly preferred means of mounting mirror 20 is to provide main housing 22 with locating tabs 23 which physically abut and position mirror 20. It will be appreciated that main housing 22 can also be integrally molded or manufactured with x-ray machine 11.

Mirror 20 can be fabricated with notches 24 to facilitate use of tabs 23, and notches 24a to allow physical placement within housing 22. Neither notches 24 or 24a are absolute limitations of the invention.

By mounting mirror 20 in main housing 22, and with main housing 22 being mounted proximate to x-ray machine 11, mirror 20 is also mounted proximate to x-ray cone 12a. Most preferably, mirror 20 is of such a size and shape and is mounted in such a position, that the entire emitted x-ray cone 12a must pass through mirror 20 before reaching target 15 as shown in FIG. 2. That is, mirror 20 encompasses x-ray cone 12a.

Mirror 20 is preferably provided with a central shoulder or step 30. Such a mirror 20 has two generally similar sections, legs or hemispheres 31 and 32 separated and connected by the stepped portion 30. Hemispheres 31 and 32 and stepped portion 30 need not be of any particular shape, although it is preferred that hemispheres 31 and 32 be semicircular to facilitate encompassing of x-ray cone 12a. Hemispheres 31 and 32 are spaced apart by stepped portion 30 and are generally parallel planar to each other although that is not required. Stepped portion 30 is of a predetermined angle relative to those planes, as is shown in the drawings. By predetermining the angle of stepped portion 30 relative to the parallel planes of hemispheres 31 and 32, the direction of light beam 14 can be predetermined, as will be more fully discussed hereinbelow. Preferably, mirror 20 is a single piece of material, hemispheres 31 and 32 being integrally formed with stepped portion 30, although this is not necessarily a limitation of the invention.

Optical mirror 20 need not be made of any particular material, but is preferably a polished aluminum mirror. Mirror 20 must be transmissive of the emitted x-rays 12a, but reflective of light beam 14. Aluminum has a particular advantage in being efficient at both the x-ray transmissivity and the light beam reflectivity, although any like material is within the scope of the invention. Mirror 20 can also be a suitable plastic substrate coated with aluminum. Examples of suitable substrates include. Most preferably, mirror 20 is transmissive to the emitted x-rays 12a to substantially the same extent over its entire surface and cross sectional area. That is, x-rays 12a passing through hemispheres 31 and 32 and stepped portion 30, as well as the union between those components, are transmitted therethrough to substantially the same degree. It is to be appreciated that the subsequent impingement of x-rays 12a upon target 15 will be substantially the same over the entire target 15 or the intended portion thereof. The resulting x-ray image is thus uniform despite there being the mirror 20 within the cone of emitted x-rays 12a.

Hemispheres 31 and 32 can be formed from a different material than stepped portion 30, as long as overall x-ray transmissivity remains the same. Hemispheres 31 and 32 need not be reflective of light beam 14 and the entire expanse of stepped portion 30 need not be reflective of light beam 14, but only that portion actually reflecting light beam 14 as will be discussed hereinbelow. It is preferred however, to fabricate mirror 20 from the same material or materials. Mirror 20 can also be a composite material and it may also be provided with any number of coatings as may be desired and common in the art.

Turning now to light beam 14, it is provided by a light beam emitter assembly generally designated by the number 21. Light emitter assembly 21 has a light emitting source 40 positioned outside the emitted x-ray cone 12a and directs a beam of focused light 14 onto stepped portion 30 of mirror 20 by generally conventional means. Stepped portion 30 reflects light beam 14 in a direction predetermined by the angle of stepped portion 30 relative to emitted light beam 14. For simplicity, although not necessarily an absolute limitation of the invention, light beam 14 exits light emitting source 40 in a direction substantially parallel to the planes of hemispheres 31 and 32. In this way however, the direction of reflected light beam 14 from stepped portion 30 is generally only determined by the predetermined angle of stepped portion 30 relative to hemispheres 31 and 32. Further, by properly positioning mirror 20, the reflected portion of light beam 14 from stepped portion 30 can be made to be approximately the same as the axial center 12 of x-ray cone 12a. Thus, the x-ray machine 11 and the emitted x-rays 12a can be properly aligned by aligning the visible light beam 14 upon target 15.

Light beam emitter assembly 21 need not be of any particular design, although it should be capable of emitting a focused beam of light 14 as was discussed hereinabove. This can be achieved in any conventional manner, including the use of appropriate optical lenses. The device 40 can also be a laser emitting device or the like, without limitation. For example only, light emitting source 40 is depicted as being a light bulb encased in a focusing lens 41 and connected to a power source (not shown) by electrical connector 42 to be powered in a conventional manner.

In use, the light emitting source 40 is caused to emit a light beam 14 focused by lens 41 to a size smaller than target 15. Light beam 14 shines onto stepped portion 30 of mirror 20 and is reflected thereby in the predetermined direction. Mirror 20 is held in place proximate to x-ray cone 12a by any means, such as by engaging hemisphere 32 with tab 23 in main housing 22. Reflected light beam 14 is caused to thereby be projected onto target 15. The x-rays of x-ray cone 12a are then caused to be emitted in a conventional manner. Because the emitted x-rays pass through optical mirror 20 in a substantially uniform manner over its entire area, the resulting x-ray image is not disturbed by the presence of optical mirror 20 within the path of x-rays 12a.

It is evident therefore, that the objects of a positioning device for an x-ray machine is carried out by the invention as herein described. All possible aspects of the invention beyond the best mode have not been necessarily described, and the scope of the invention shall only be determined by the following claims.

I claim:

1. A device for positioning the location of an emitted x-ray from an x-ray emitting device and relative to an x-ray target, comprising:

an optical mirror having at least two leg portions separated by a stepped portion integrally formed with said leg portions and positioned at a predetermined angle thereto; said leg portions and said stepped portion having substantially uniform x-ray transmissivity;

a light emitting means for transmitting a locating beam of light onto said stepped portion of said optical mirror, said beam of light having a diameter of up to about 0.5 inches; and mounting means for mounting said optical mirror proximate to the x-ray emitting device and completely encompassing the emitted x-ray;

such that said locating beam of light is caused to be directed toward the x-ray target based upon said predetermined angle.

2. A device as in claim 1, wherein said light emitting means emits a beam of light the same size or smaller of the x-ray target.

3. A device as in claim 1 wherein said light emitting means emits a beam of light in a direction substantially concurrent with the axial center of the emitted x-ray.

4. A device as in claim 1 wherein said optical mirror leg portions are hemispherical and parallel planar.

5. A method of aligning the path of an emitted x-ray relative to an x-ray target, comprising the steps of:

providing an optical mirror having first and second leg portions separated and connected by a stepped portion at a predetermined angle thereto;

projecting a light beam having a diameter of up to about 0.5 inches onto said stepped portion such that the light beam is reflected from said stepped portion and is projected upon the x-ray target.

6. An improved dental x-ray positioning device for adjusting the path of an emitted x-ray relative to an x-ray target, of the type having an optical mirror placed at an angle within an x-ray emission, and having a remote light source for projecting a light beam onto the optical mirror, the improvement comprising:

said optical mirror being positioned to completely encompass the emitted x-ray; and said optical mirror having first and second leg portions separated and connected by an integrally formed angled and stepped portion; said first and second leg portions and said stepped portion having a substantially uniform transmissivity to the x-ray emission, and said light beam having a diameter of up to about 0.5 inches.

7. An improved positioning device as in claim 6, wherein said light emitting means emits a beam of light the same size or smaller of the x-ray target.

8. An improved positioning device as in claim 6 wherein said light emitting means emits a beam of light in a direction substantially concurrent with the axial center of the emitted x-ray.

9. An improved positioning device as in claim 6 wherein said optical mirror leg portions are hemispherical and parallel planar.

* * * * *